US 9,855,005 B2

(12) United States Patent
Cheng

(10) Patent No.: US 9,855,005 B2
(45) Date of Patent: Jan. 2, 2018

(54) WEARABLE POSTURE ADVISORY SYSTEM

(71) Applicant: Samsung Electronics Co., Ltd., Suwon-si, Gyeonggi-do (KR)

(72) Inventor: Doreen Cheng, San Jose, CA (US)

(73) Assignee: Samsung Electronics Co., Ltd., Suwon-si (KR)

( * ) Notice: Subject to any disclaimer, the term of this patent is extended or adjusted under 35 U.S.C. 154(b) by 291 days.

(21) Appl. No.: 14/693,705

(22) Filed: Apr. 22, 2015

(65) Prior Publication Data

US 2016/0310064 A1    Oct. 27, 2016

(51) Int. Cl.
*A61B 5/103* (2006.01)
*A61B 5/117* (2016.01)
*A61B 5/00* (2006.01)
*A61B 5/11* (2006.01)
*G05B 19/4099* (2006.01)
*B29C 67/00* (2017.01)
(Continued)

(52) U.S. Cl.
CPC .......... *A61B 5/4561* (2013.01); *A61B 5/1116* (2013.01); *A61B 5/486* (2013.01); *G05B 19/4099* (2013.01); *A61B 5/107* (2013.01); *A61B 5/1077* (2013.01); *A61B 5/1079* (2013.01); *A61B 5/6804* (2013.01); *A61B 5/6805* (2013.01); *A61B 5/6823* (2013.01); *A61F 5/024* (2013.01); *A63B 23/0244* (2013.01); *A63B 2230/62* (2013.01); *B29C 67/0088* (2013.01); *B33Y 50/02* (2014.12); *B33Y 80/00* (2014.12); *G05B 2219/35134* (2013.01); *G05B 2219/49007* (2013.01); *G08B 21/0446* (2013.01)

(58) Field of Classification Search
CPC ..... A61B 5/107; A61B 5/1077; A61B 5/1079; A61B 5/1116; A61B 5/4561; A61B 5/6804; A61B 5/6805; A61B 5/6823; B33Y 50/02; G08B 21/0446; A61F 5/024; A63B 23/0244; A63B 2230/62; B29C 67/0051
See application file for complete search history.

(56) References Cited

U.S. PATENT DOCUMENTS 5,398,697 A    3/1995  Spielman
5,749,838 A    5/1998  Kline
(Continued)

FOREIGN PATENT DOCUMENTS

CN    104385589    3/2015

OTHER PUBLICATIONS

International Search Report dated Jul. 20, 2016 from PCT Application No. PCT/KR2016/003771.

*Primary Examiner* — Devin Henson
(74) *Attorney, Agent, or Firm* — Beyer Law Group LLP

(57) ABSTRACT

In one aspect, a method for formulating a wearable posture advisory system will be described. A three dimensional body model of at least a part of a body of a user is obtained. A model for 3D printing a wearable posture advisory system is generated based on the 3D body model. The system model models one or more sensors that are arranged to help determine a posture of a user and one or more actuators that are arranged to help instruct the user to adjust his or her posture. The system model is provided to a 3D printer so that the 3D printer can print the wearable posture advisory system. Various embodiments relate to devices, arrangements and executable computer code that are associated with the above method.

11 Claims, 12 Drawing Sheets

(51) Int. Cl.
*B33Y 50/02* (2015.01)
*A61B 5/107* (2006.01)
*A63B 23/02* (2006.01)
*G08B 21/04* (2006.01)
*A61F 5/02* (2006.01)
*B33Y 80/00* (2015.01)

(56) References Cited

U.S. PATENT DOCUMENTS

| | | |
|---|---|---|
| 5,866,818 A | 2/1999 | Sumi et al. |
| 6,544,203 B2 | 4/2003 | Hazard |
| 6,827,694 B2 | 12/2004 | Gladoun |
| 7,141,026 B2 | 11/2006 | Aminian et al. |
| 7,308,332 B2 | 12/2007 | Okada et al. |
| 7,433,753 B2 | 10/2008 | Okada et al. |
| 7,843,351 B2 | 11/2010 | Bourne et al. |
| 8,011,229 B2 | 9/2011 | Lieberman et al. |
| 8,018,346 B2 | 9/2011 | Gottlieb et al. |
| 8,200,340 B2 | 6/2012 | Skelton et al. |
| 8,203,455 B2 | 6/2012 | Lee et al. |
| 8,217,797 B2 | 7/2012 | Ikoyan |
| 8,437,861 B2 | 5/2013 | Skelton et al. |
| 8,447,411 B2 | 5/2013 | Skelton et al. |
| 8,613,716 B2 * | 12/2013 | Summit .................. A61F 5/013 602/19 |
| 2003/0135134 A1 | 7/2003 | Chase et al. |
| 2005/0107722 A1 | 5/2005 | Ozaki et al. |
| 2007/0010768 A1 | 1/2007 | Simanovsky |
| 2007/0233311 A1 | 10/2007 | Okada et al. |
| 2008/0312516 A1 | 12/2008 | Ozaki et al. |
| 2009/0315721 A1 | 12/2009 | Gottlieb et al. |
| 2010/0010574 A1 | 1/2010 | Skelton et al. |
| 2010/0010583 A1 | 1/2010 | Panken et al. |
| 2010/0078977 A1 | 4/2010 | Glyck |
| 2010/0138193 A1 | 6/2010 | Summit et al. |
| 2010/0228488 A1 | 9/2010 | Leuthardt et al. |
| 2010/0268138 A1 | 10/2010 | Summit et al. |
| 2011/0063114 A1 | 3/2011 | Ikoyan |
| 2012/0116477 A1 | 5/2012 | Crowe et al. |
| 2012/0203140 A1 | 8/2012 | Malchau et al. |
| 2012/0245491 A1 | 9/2012 | Amell et al. |
| 2013/0015976 A1 | 1/2013 | Chang et al. |
| 2013/0043999 A1 | 2/2013 | Van Beest |
| 2013/0204169 A1 | 8/2013 | Poepperling et al. |
| 2013/0274830 A1 | 11/2013 | Skelton |
| 2013/0317400 A1 | 11/2013 | Ferezy |
| 2014/0081190 A1 | 3/2014 | Summit et al. |
| 2014/0200496 A1 * | 7/2014 | Hyde .................. A61F 5/32 602/19 |
| 2014/0243721 A1 | 8/2014 | Bryant |
| 2014/0277663 A1 | 9/2014 | Gupta et al. |
| 2015/0250420 A1 * | 9/2015 | Longinotti-Buitoni A61B 5/6804 600/301 |
| 2016/0349738 A1 * | 12/2016 | Sisk .................. B29C 67/0085 |

* cited by examiner

WEARABLE POSTURE ADVISORY SYSTEM

FIELD OF THE INVENTION

The present invention relates generally to wearable technologies. More specifically, the present invention relates to a wearable posture advisory system that provides guidance on how to maintain a desired posture.

BACKGROUND

Posture is an important component of good health. If a proper posture is not maintained, a wide variety of medical problems can arise. For example, poor posture can sometimes cause chronic back pain, which is a leading cause of disability in the United States.

However, it can be difficult to maintain a proper posture. Many individuals work at jobs that require a person to sit in a chair and work with a computer for hours on end. Other jobs can involve a great deal of lifting, bending or standing. Such jobs can easily lead to poor posture and associated neck, back and shoulder problems. Although books and consultants are available to provide tips on maintaining a proper posture, it is all too easy to forget such tips in the midst of a busy workday. Some people, who suffer from both poor posture and chronic pain, visit physical therapists and other specialists who help to alleviate some of the pain and correct the posture. However, visiting specialists on a regular basis can be time-consuming and expensive. As a result, there are ongoing efforts to find better ways to assist people in maintaining a proper posture and other healthy habits.

SUMMARY

In one aspect, a method for formulating a wearable posture advisory system will be described. A three dimensional body model of at least a part of a body of a user is obtained. A model for 3D printing a wearable posture advisory system is generated based on the 3D body model. The system model models one or more sensors that are arranged to help determine a posture of a user and one or more actuators that are arranged to help prompt the user to adjust his or her posture. The system model is provided to a 3D printer so that the 3D printer can print the wearable posture advisory system. In various embodiments, the above method is stored in a computer readable storage medium in the form of executable computer code.

In another aspect, a wearable posture advisory system is described. The system includes a wearable material that is arranged to be worn by a user. The system further includes one or more active elements, which are positioned on the wearable material. Each active element includes one or more of a sensor and an actuator. When the wearable posture advisory system is worn by a user, the active elements may be arranged over the body of the user in a wide variety of ways. In some embodiments, for example, the active elements are distributed asymmetrically or unevenly to help concentrate the active elements on areas of particular concern.

BRIEF DESCRIPTION OF THE DRAWINGS

The invention and the advantages thereof, may best be understood by reference to the following description taken in conjunction with the accompanying drawings in which.

In the drawings, like reference numerals are sometimes used to designate like structural elements. It should also be appreciated that the depictions in the figures are diagrammatic and not to scale.

DETAILED DESCRIPTION

Figure 1:
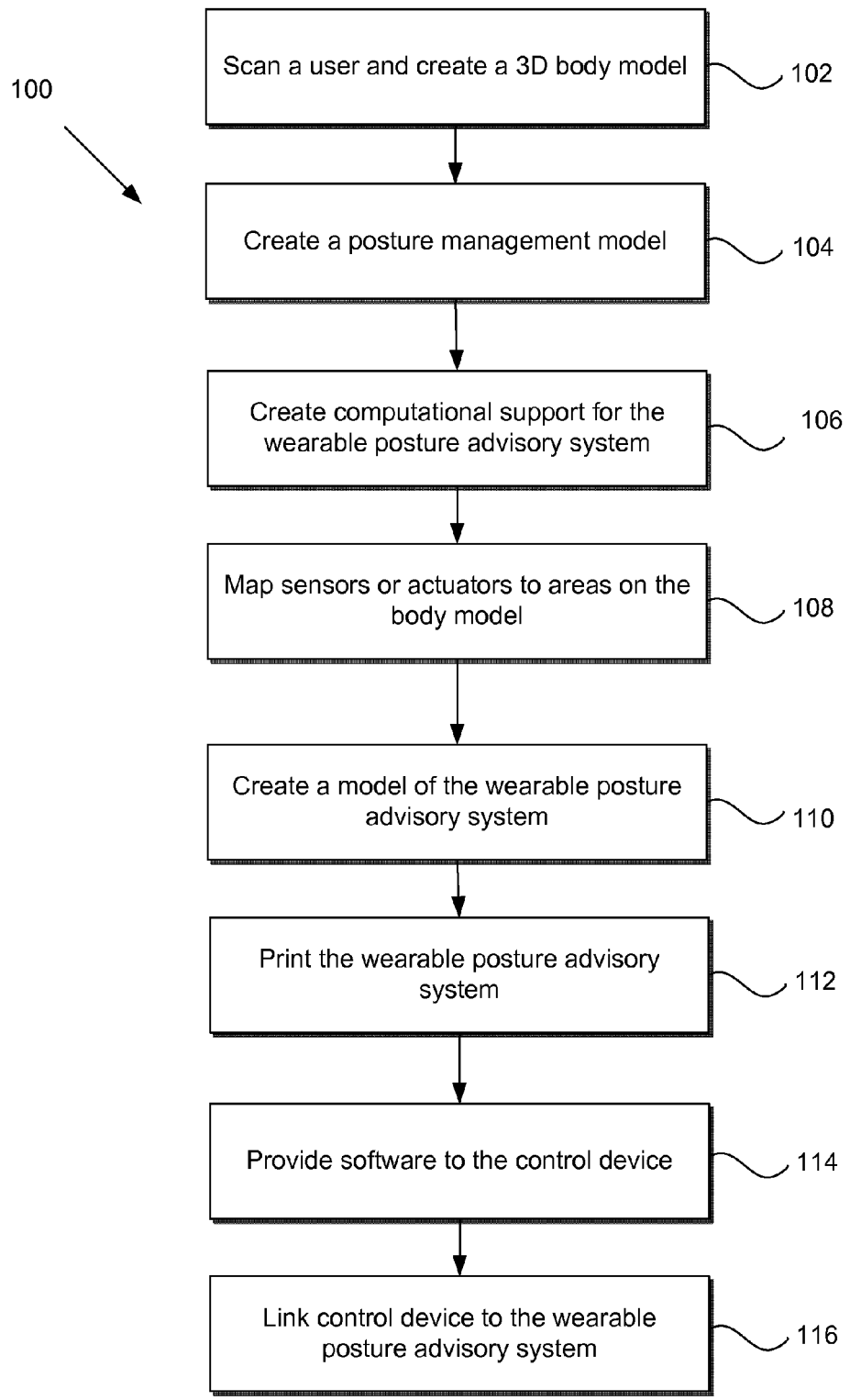
FIGS. 1-2 are flow diagrams illustrating methods for managing and manufacturing a wearable posture advisory system according to a particular embodiment of the present invention.

The present invention relates to methods and arrangements for managing and improving posture. More specifically, various embodiments of the present invention relate to a wearable posture advisory system that is tailored to the physical characteristics of a particular user.

As noted in the Background, it is well known that maintaining a proper posture is essential to good health. However, many people find it very difficult to maintain a good posture. A typical workday can involve a great deal of sitting, lifting or bending, which places stresses on the body and makes it easy to forget the importance of a good posture.

One way of reminding a user to maintain a correct posture is to use a wearable device. By way of example, the device may be attached to or worn by the user. The device includes multiple sensors that are placed on various parts of the body. The sensors monitor the user's posture and detect when the posture of the user has changed for the worse. At that point, the device would remind the user to correct his or her posture, perhaps by vibrating, asserting pressure, emitting heat, or emitting an audio signal.

One approach to distributing such devices would be to manufacture identical devices and distribute or sell them to the general population. That is, each customer would receive the same device. This approach, however, has some limitations. People can have very different physical characteristics (e.g., heights, weights, dimensions, etc.) The sensors of the device, for example, may have to be distributed in a different pattern for one person than for another person. A generic, one-size-fits-all device may have difficult adapting to a wide variety of different body types.

Also, it should be appreciated that the techniques or methods used to maintain a good posture may not be the same for every user. That is, a particular posture that is ideal of one person may be suboptimal or even harmful to another person. For example, it may be ideal for a particular person to sit up straight. However, for another person it may be best to assume a sitting posture that involves a slight bend in the back. Such a person may have been in an accident or have a condition that makes it difficult or impossible to assume a more straight posture. If the device does not take such differences into account, the user may receive improper guidance from the device.

Various implementations of the present invention address one or more of the above issues. In some embodiments of the present invention, a wearable posture advisory system is created based on a three dimensional (3D) body scan. The wearable posture advisory system is then printed using a 3D printer. In some embodiments, each system is thus highly customized for a particular user and/or takes into account unique physical characteristics of the user. In other embodiments, identical devices are customized for and distributed to a particular population that has similar physical characteristics (e.g., similar needs, sizes, shapes, etc.)

Figure 2:
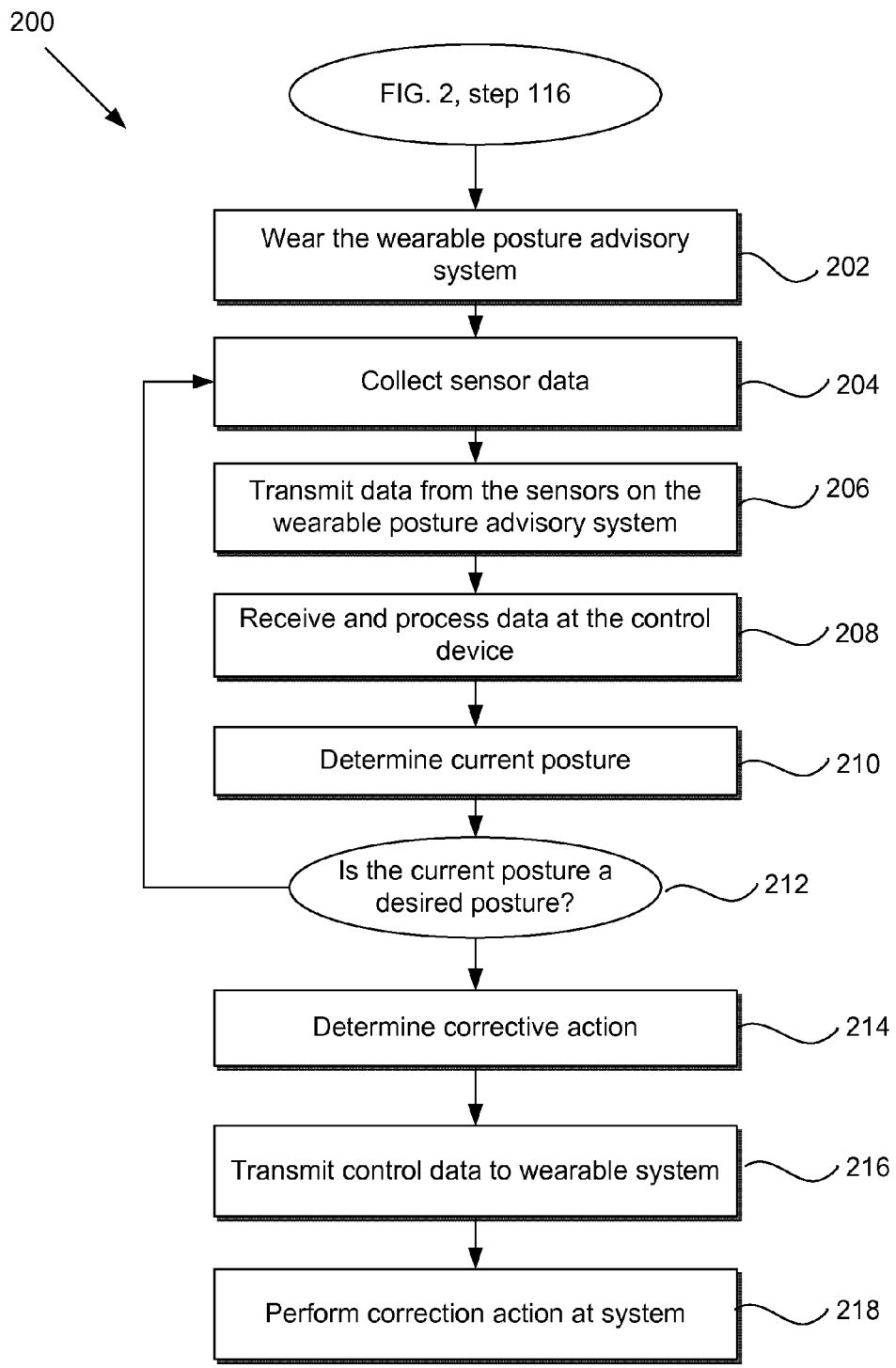
Figure 3:
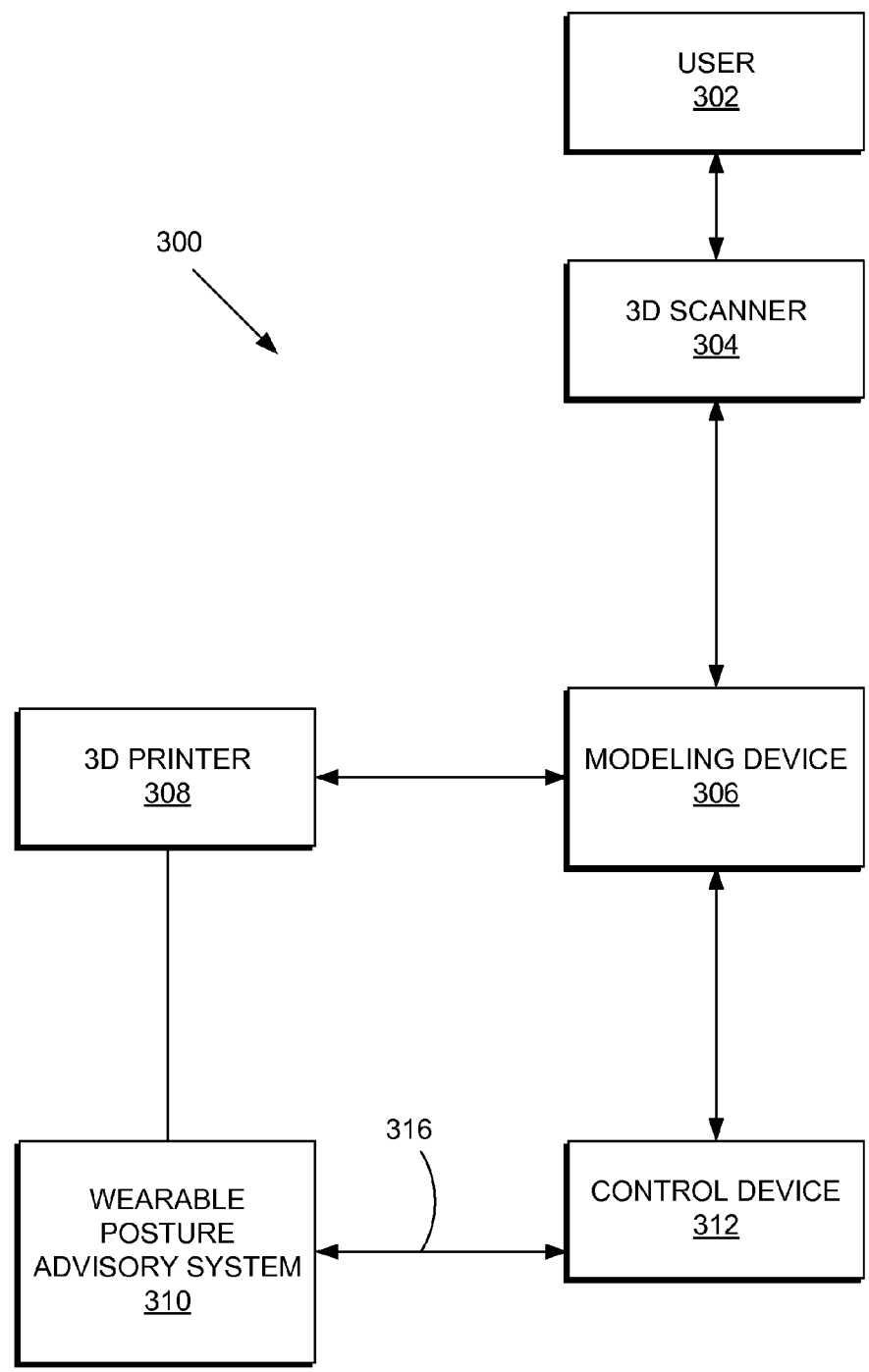
FIG. 3 is a block diagram of a system for managing and manufacturing a wearable posture advisory system according to a particular embodiment of the present invention.

Referring now to FIGS. 1-3, example methods 100 and 200 for manufacturing and managing a wearable posture advisory system will be described. The methods 100 and 200 of FIGS. 1 and 2 are performed using the system 300 illustrated in FIG. 3. The system 300 includes a variety of components, including a three dimensional (3D) scanner 304, a 3D printer 308, a modeling device 306, a control device 312 and a wearable posture advisory system 310 that is printed by the 3D printer 308.

It should be noted that the methods 100 and 200 describe various operations that may be performed by a particular component or device in FIG. 3. However, it should be appreciated that any operation performed by one device may instead be performed by a different device, or another device not shown in FIG. 3. That is, the operations of methods 100 and 200 may be performed by fewer or more devices than are shown in FIG. 3.

Initially, at step 102 of method 100 of FIG. 1, a three dimensional (3D) scanner 304 scans a body or a part of a body of a user 302 and generates a three dimensional model of the scanned body or body part. The 3D scanner 304 may include any suitable device or devices that are associated with the scanning of an object to help generate a three dimensional model of the object. Any known 3D scanning technologies and techniques may be used to scan a body or body part and generate an associated body model. Such technologies may include but are not limited to laser scanners, contact scanners, non-contact scanners, conoscopic holography, structured light and modulated light scanners.

Figure 4:
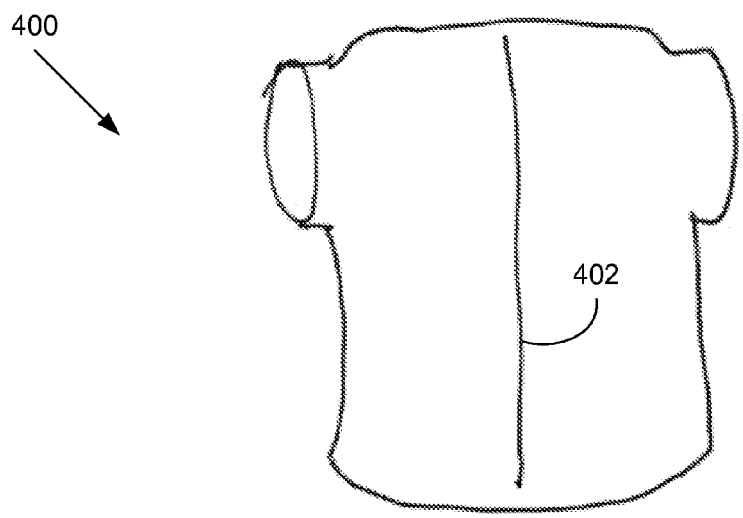
FIGS. 4-6 illustrate example three dimensional body models and postures according to various embodiments of the present invention.

FIG. 4 illustrates an example of a simplified 3D body model 400 that has been generated based on the 3D scanning of a person's trunk e.g., upper back and torso. The body model 400 indicates the location of surfaces or points in three dimensional space that correspond to the surface and contours of the scanned trunk. That is, the body model 400 indicates at least in part the three dimensional shape or form of the scanned trunk.

Body model 400 represents a generic torso and back with a straight posture, as indicated by a midline 402 that corresponds to the alignment of the spine. However, the physical characteristics of users may differ considerably, and the associated body models may reflect these differences. By way of example, FIG. 4 illustrates another example body model 500 in which the trunk is slightly curved, as indicated by the curved midline 502. The scanning and modeling process can effectively capture various physical attributes and forms that depart from a generic, idealized or reference body shape.

In the example illustrated in FIGS. 1-3, a modeling device 306 receives the 3D model from the 3D scanner 304 and/or generates the 3D model based on data received from the 3D scanner 304. The modeling device 306 may be any suitable computing device, including but not limited to a personal computer, a laptop, a wearable device and/or a portable device such as a smartphone. Returning to FIG. 1, at step 104, the modeling device 306 generates a posture management model based on the 3D body model. The posture management model is a model that helps define a desired (e.g., ideal, normal or healthy) posture, one or more alternative postures that are different from the desired posture, and one or more corrective actions that a user can undertake to transition from an alternative posture to the desired posture. The posture management model may be generated using any suitable software or hardware. Generally, the posture management model is based on the 3D body model created in step 102 and thus takes into account individual physical characteristics of a user.

Any suitable technology or techniques may be used to determine the posture management model. In various embodiments, the posture management model is arranged to help determine a variety of postures that the user may take up, including a desired posture and an alternative posture. Generally, the desired posture represents a posture that is beneficial to the user e.g., that provides ergonomic and medical benefits for the user. For example, the desired posture may involve sitting up fairly straight or in a manner that allows the muscles to relax rather than remain imbalanced. As previously noted, however, the ideal, desired posture may differ, depending on the person.

By way of example, the posture 404 indicated by the body model 400 in FIG. 4 may represent an ideal, desired posture for some people. The posture 404 indicates a fairly straight back and spine. However, some people, due to injury or a medical condition, cannot easily or safely assume such a posture for long periods of time. An example of this is the posture 504 indicated in FIG. 5 by body model 500. Posture 504 represents a trunk and a spine that is slightly tilted to the right. It is possible that for a particular person, such a tilt is the ideal, desired posture, since attempting to further straighten the spine would cause fatigue and even injury. Thus, for the purpose of this simplified example, the orientation, shape and/or angle of body model 500 also represents the desired posture 504 for a particular user in the posture management model.

In addition to the desired posture, the modeling device also is arranged to determine one or more alternative postures. Each alternative posture is a posture that deviates from the desired posture. Some or all of these alternative postures may be somewhat suboptimal from the standpoint of the user's overall health. In some implementations, the modeling device 306 determines a range of different alternative postures that the user is most likely to assume during the day.

Figure 5:
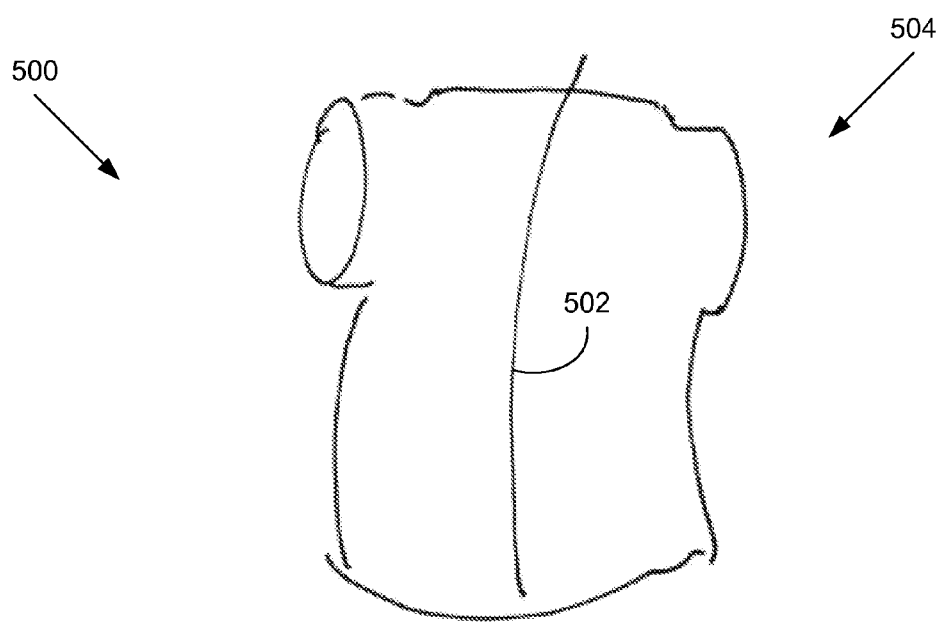
Figure 6:
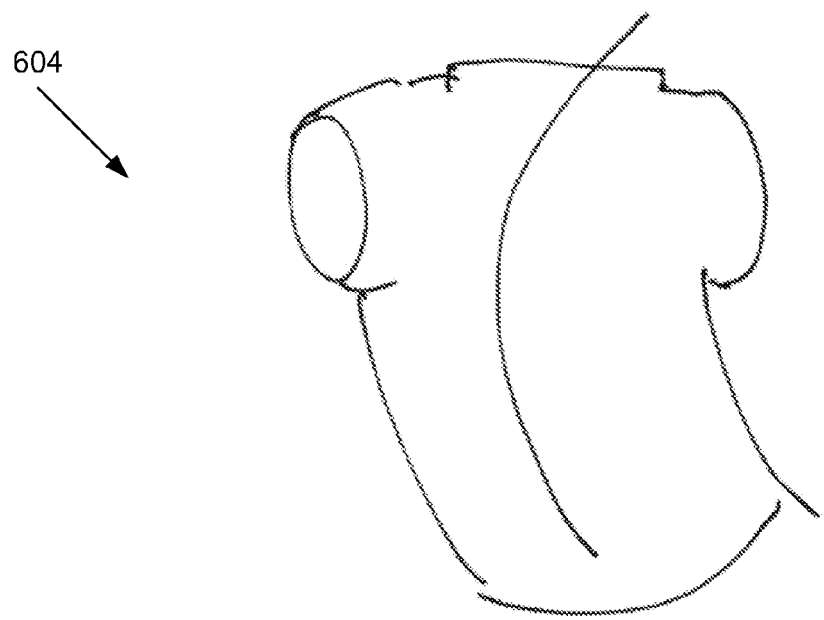

FIG. 6 represents an example alternative posture 604. As indicated in the figure, alternative posture is different from desired posture 504 of FIG. 5. That is, the curve in the torso is more pronounced, possibly suggesting that the user is leaning on an arm of a chair or against a table.

Figure 7:
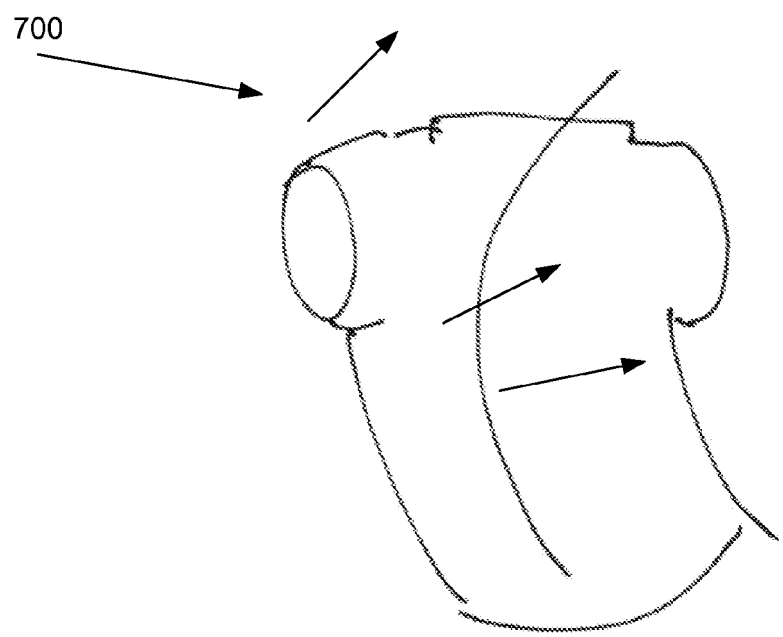
FIG. 7 illustrates a corrective action according to a particular embodiment of the present invention.

The modeling device 306 is also arranged to determine a corrective action. The corrective action is an action that can be undertaken by a user to shift from an alternative posture to an optimal position. An example of a correction action 700 is shown in FIG. 7. In the figure, directional arrows indicate how a user could move portions of his or her body so that the posture would better resemble the desired posture.

In some embodiments, the corrective action is determined based at least in part on the degree and direction of the deviation between the desired posture and a particular alternative posture. That is, the larger the deviation, the stronger the corrective action. By way of example, if the deviation is large (e.g., the user is in a contorted position that is very far from the desired posture), the corrective action may involve a larger corrective motion (e.g., involving a greater amount of motion or effort) on the part of the user. Accordingly, in various embodiments, when the deviation is greater, a wearable posture advisory system being worn by the user at the time emits a stronger stimulus (e.g., stronger vibration, higher temperature, stronger pressure, a louder audio signal, etc.) to the user than if the deviation were smaller. (The stimulus may be commanded and applied as later described in steps 214-218 of FIG. 2.)

It should be appreciated that information related to the desired posture(s), the alternative posture(s) and the corrective action(s) may be stored and arranged in any suitable manner. Any data that helps indicate or model the above postures and actions may form part of the posture management model. In some embodiments, for example, the posture management model is stored in the form of three dimensional body models, which help indicate the aforementioned postures and corrective actions. In still other embodiments, the posture management is stored at least in part in the form of coordinates, which reference regions of a body, help identify the position of those regions in a given posture and/or also help indicate how such regions should be changed or moved to achieve the desired posture.

The posture management model may be configured and adjusted in a variety of ways. In some approaches, for example, the posture management model is generated based on the 3D body model and thus automatically takes into account the unique physical characteristics of the user. In other embodiments, the posture management model is based on a predefined, generic concept of what should constitute a desired posture, alternative postures and various corrective actions (e.g., concepts based on an ideal or reference human body). The posture management model is stored in a computing device (e.g., the modeling device 306). A specialist (e.g., a physical therapist, a doctor, etc.) can then use the computing device to adjust aspects of the posture management model based on an examination of and consultation with the user. For example, if the user has a slight bend in the back caused by a medical condition or accident that, in the specialist's judgment, should not be completely straightened, the specialist may adjust the model's definition of a desired posture from a completely straight posture to a slightly bent posture. A software editing tool can be provided to the specialist for quick and easy adjustments.

Returning to FIG. 1, at step 106, the modeling device 306 generates computational support using the 3D body model. This computational support is any system for mapping or associating functions, features or elements of a wearable posture advisory system to one or more parts of the body. The computational support may take a wide variety of forms. In some embodiments, for example, the computational support is in the form of a mesh, graph, network or lattice that is overlaid on or references different portions of the 3D body model.

Figure 8:
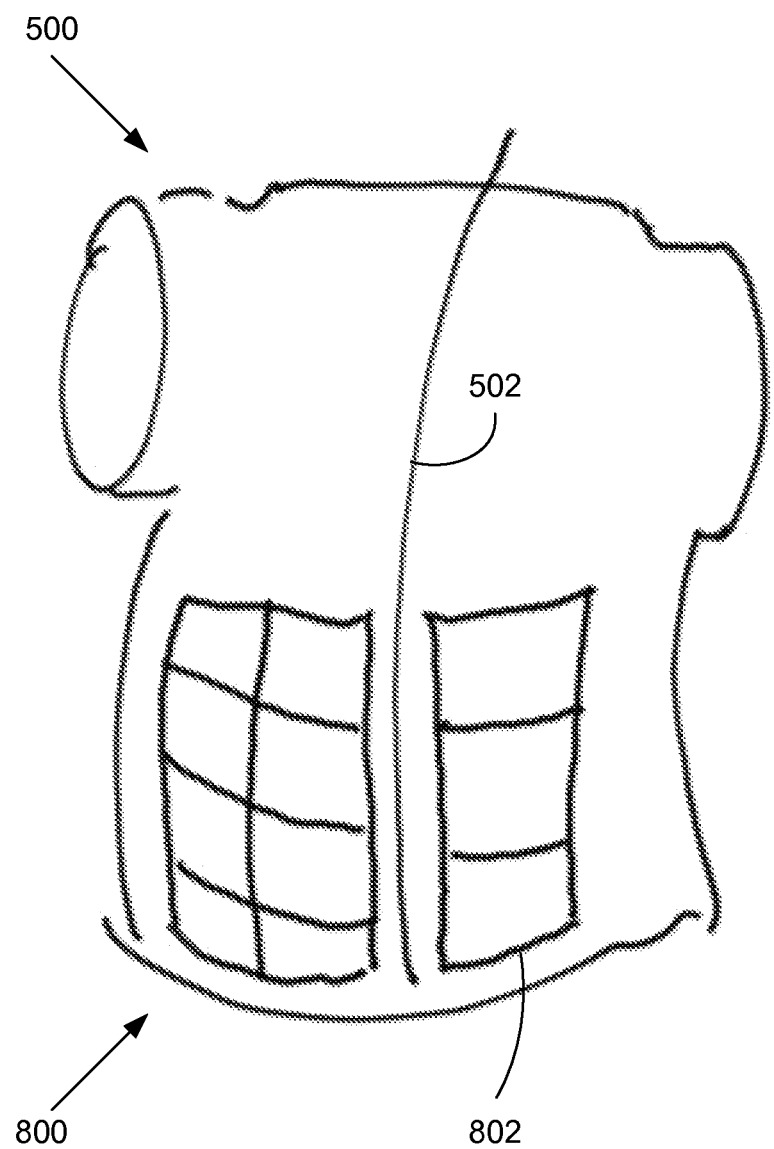
FIGS. 8-9 illustrate an example body model with a mesh and active elements superimposed over the model.

FIG. 8 illustrates a simplified example of the above approach. In FIG. 8, the computational support takes the form of a mesh 800. The mesh includes multiple cells 802. Each cell 802 is associated with a distinct portion of the body model 500. The cell 802 may take any suitable form. In the illustrated embodiment, for example, each cell has a particular shape (e.g., any geometric shape, such as a rectangle, square, hexagon, etc.). The cells may be positioned adjacent to one another to form an array or lattice.

Some implementations involve a particular association between each cell and a particular component of a wearable posture advisory system. In the illustrated embodiment, for example, each cell is associated with a different sensor. (It should be appreciated that in other embodiments each cell can be associated with any component illustrated in FIGS. 13 and 14.) In some implementations, each cell corresponds to a unique address (e.g., label, ID etc.) As a result, the location and identity of any components located at a cell can be readily identified using the address.

The cells may be arranged in any suitable configuration or format. The cells need not be arranged evenly across any region of the body model. In the illustrated embodiment of FIG. 8, for example, the cells 802 are arranged asymmetrically relative to the spine of the body or the line of symmetry of the body (i.e., a midline that runs down the middle of the body/body model and divides it into two substantially symmetrical parts.) That is, there are far more cells on the left side of the midline 502/spine than the right side. Also, the cells on the left side are smaller and have a higher density for a region of a particular size then the cells on the right side. Having a higher cell density can indicate that there is a medical or computational need for there to be more electronic components (e.g., sensors, actuators of the wearable posture advisory system) in one part of the body than another part of the body, if it is assumed that each cell corresponds to a predefined number of electronic components (e.g., one sensor or active element per cell, etc.)

Figure 9:
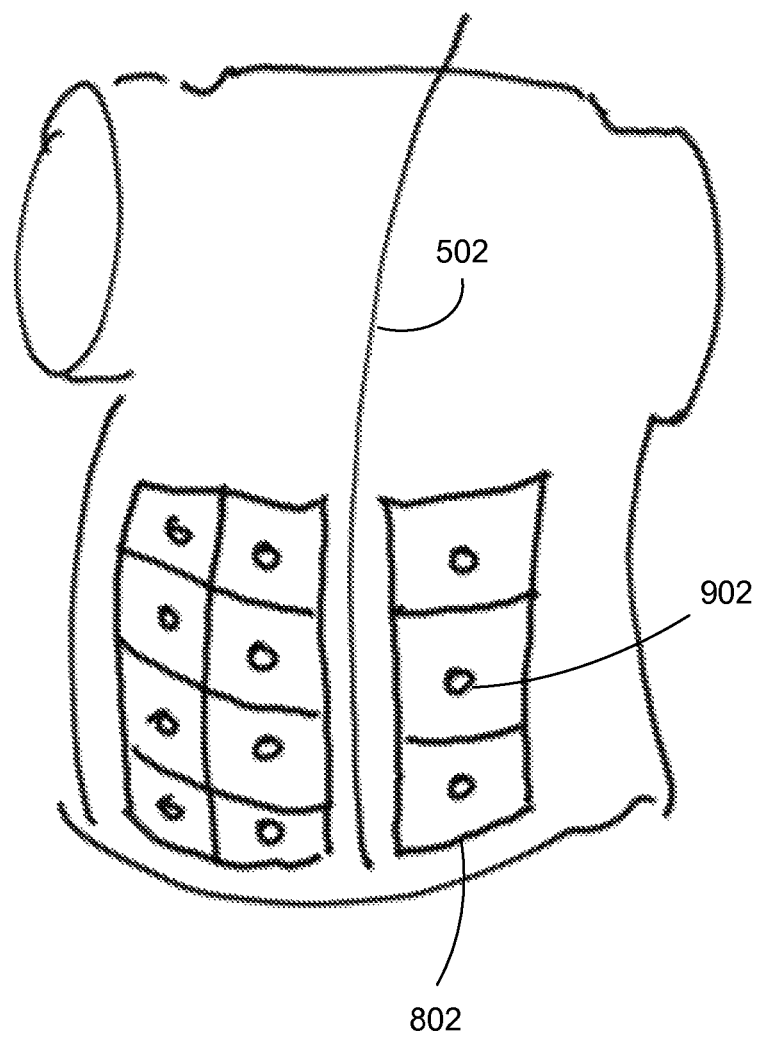

Optionally, at step 108 of FIG. 1, each cell 802 is mapped to one or more components of a contemplated wearable posture advisory system. That is, each cell 802 and its unique address is associated with one or more components (e.g., actuators, sensors, transceivers, etc.) of a wearable posture advisory system. In the illustrated embodiment of FIG. 9, for example, each cell 802 is now associated with an active element 902. Each active element 902, in turn, contains a distinct sensor.

The way in which the components and corresponding cells are arranged may be based on the posture management model and the 3D body model. That is, the arrangement may take into account the physical characteristics and medical needs of the user. For example, in the example illustrated in FIG. 9, the sensors and cells 802 in the illustrated embodiment are distributed unevenly. That is, in this example, relative to a midline 502/spine, the sensors are arranged asymmetrically relative to the spine. There are more sensors and a greater density of sensors (i.e., more sensors for a region of the same size) on the left side of the spine than the right side.

One reason for this may be the postural tendencies of the user. That is, the posture management model, as illustrated in the examples of FIGS. 5-7, indicates that the user tends to bend his or her torso towards the right. As a result, there is typically greater stretching or tension in the left side of the lower back muscles of the user than in the right side. In some embodiments, to properly track physical changes in the muscles on the left side of the user, the mesh and planned wearable posture advisory system contemplate having more sensors and electronic components on the left side rather than the right side. Of course, the rationale for placing more sensors or electronic components on a particular part of the body will vary, depending on the posture, medical condition and/or physiology of the user.

Based on the mapping process performed in step 108, the 3D body model and/or the posture management model, the modeling device 306 then generates a three dimensional model of the wearable posture advisory system (step 110). The system model is any suitable model that helps indicate the dimensions and structure of the wearable posture advisory system 310. In various implementations, the 3D system model indicates the relative location of various components of the system, including any sensors, actuators, active elements, electronic components, transceivers, networking elements, straps, bands, etc. Any known 3D modeling software or hardware (e.g., any suitable computer aided design tool) may be used to generate the system model.

Figure 10:
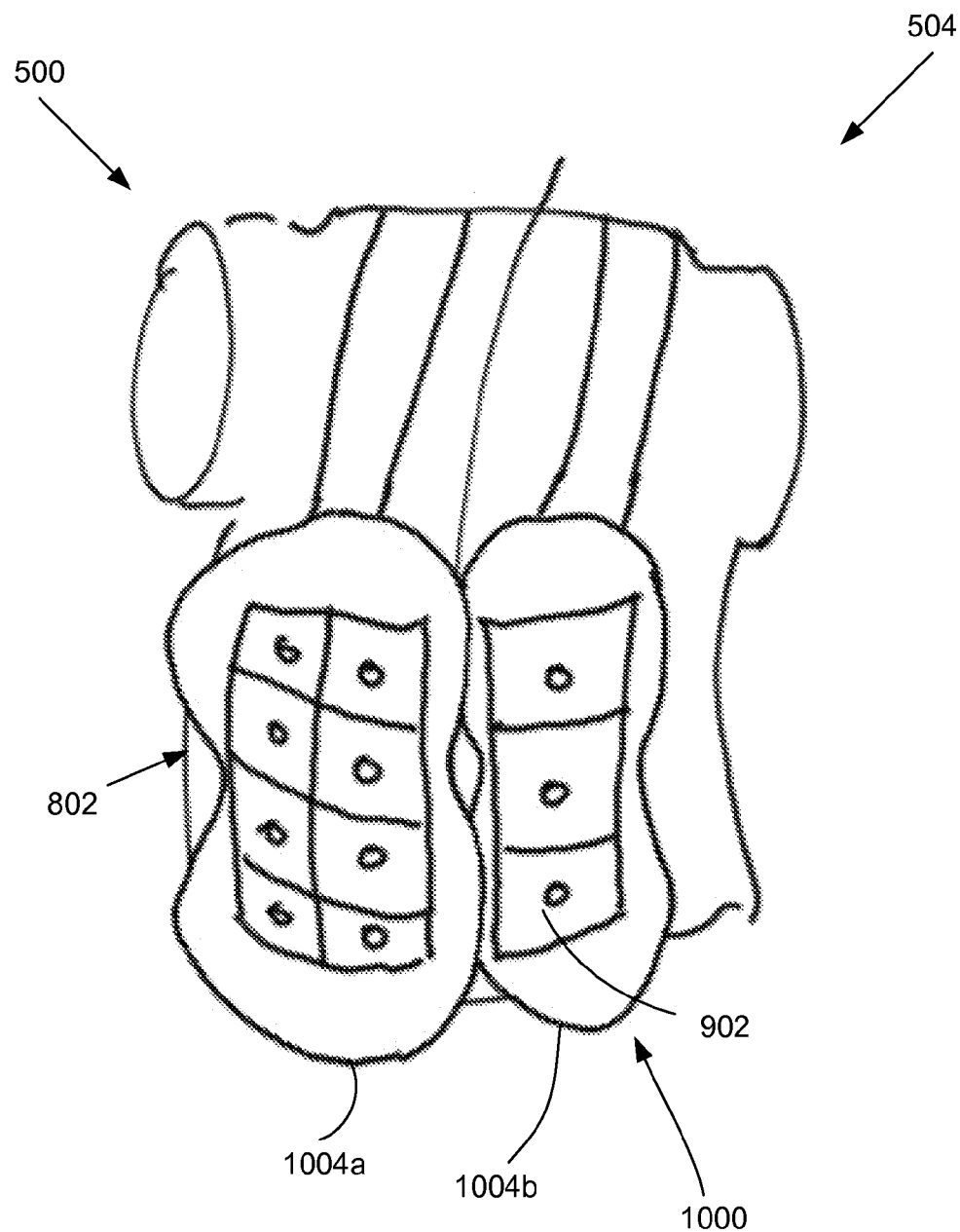
FIG. 10 illustrates a three dimensional model of a wearable posture advisory system according to a particular embodiment of the present invention.

An example of such a model is illustrated in FIG. 10. FIG. 10 illustrates a three dimensional model 1002 of a wearable posture advisory system 310 including two strips 1004a/1004b. The two strips 1004a/1004b each include active elements 902. Each active element 902 includes an arrangement of one or more sensors, actuators, networking elements, circuits, fabric elements, cloth elements and/or other components. (Some of these components are described in greater detail later in the application.) The 3D body model 500 and its associated mesh 802 is also illustrated in FIG. 10 in order to convey an example of how the wearable posture advisory model can associate each component with a particular portion of the user's body model/body.

The dimensions and locations of the components of the wearable posture advisory model may take into account the shape and dimensions of the 3D body model and the cells used in the mesh. In the illustrated embodiment, for example, each active element 902 in the system model 1000 is associated with a cell 802 in the mesh 802. The contours and shape of the strips 1004a/1004b are designed to follow the contours and shape of the torso depicted in the 3D model 500. In this particular example, the two strips 1004a/1004b are configured to be worn around the lower back region of a person, with each pad being placed flush against regions that are adjacent to and on either side of the spine.

The system model 1000 can be quite detailed. In various designs, for example, the system model 1000 describes and indicates numerous features of almost every component in the wearable posture advisory system 310 including the material(s) each component is made of, the dimensions of each component, the exact location of each component relative to the rest of the system, the conductive and/or non-conductive materials (e.g., wires, straps, etc.) that connect the components, etc. In various embodiments, the system model 1000 is sufficiently detailed such that it can be used to help manufacture the wearable posture advisory system 310 e.g., using a three dimensional printer 308.

After the 3D system model is generated, it is provided to a 3D printing device 308. The 3D printing device 308 then prints the wearable posture advisory system 310 based on the 3D system model 1000 (step 112 of FIG. 1) The printed system 310 has the components, structure, shape, dimensions, materials and/or design as defined in the 3D system model 1000.

The printing of the system 310 may require various analytical or processing steps. In some embodiments, for example, the 3D system model 1000 is stored in a file that needs to be converted to a new format (e.g., .STL, .OBJ) so that the 3D printer 308 can read the file. Software is used to divide up the 3D system model into multiple thin slices or layers. The materials used to form each thin layer are identified. The 3D printer 308 then successively deposits the layers using the identified materials to gradually build the system 310 as indicated in the system model 1000.

Any known 3D printer 308 may be used to print the wearable posture advisory system 310. Generally, the 3D printer 308 uses additive manufacturing techniques. That is, layers of material are sequentially applied over one another to gradually form the system 310. In some implementations, it should be noted that both conductive/electrical components (e.g., for sensors, actuators, electronics, etc.) as well as non-conductive components (e.g., plastic or fabric materials) may be deposited using the same 3D printer 308. The use of the 3D printer 308 enables the user to rapidly manufacture a wearable posture advisory system 310 that is tailored to his or her physical shape, condition and/or characteristics.

Figure 11:
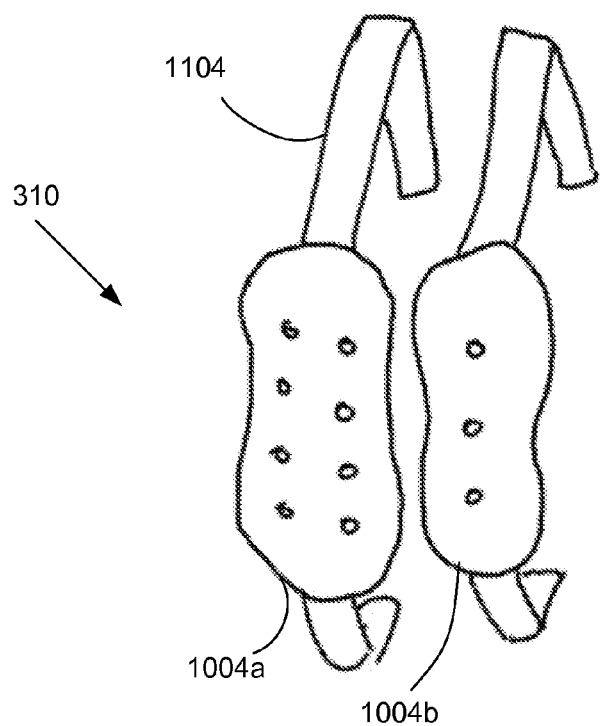
FIGS. 11-12 illustrate example wearable posture advisory systems according to various embodiments of the present invention.
Figure 12:
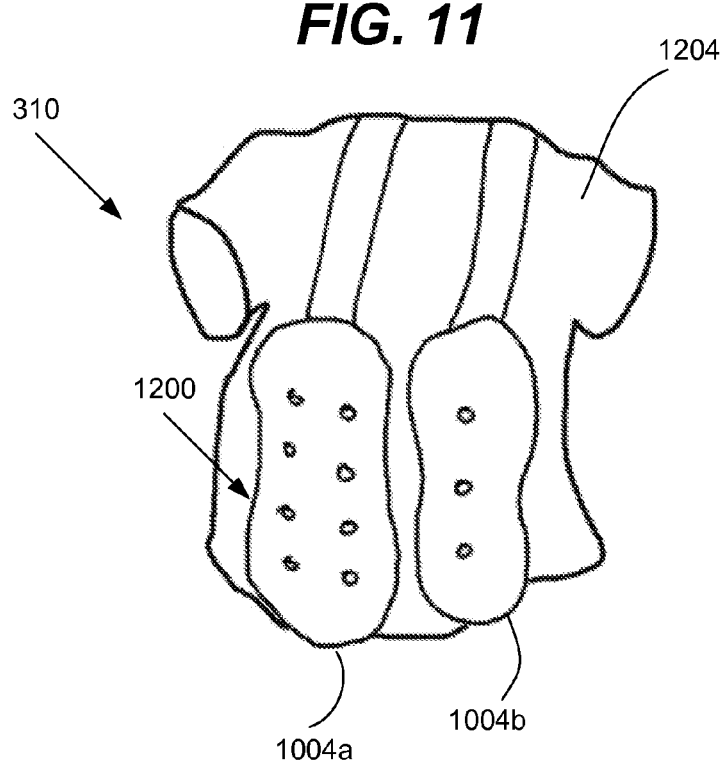

The 3D printer 308 may generate a wide variety of different designs that may or may not require additional manufacturing steps to create a finished, wearable product. FIGS. 11 and 12 illustrates two example approaches. In FIG. 11, the 3D printer 308 prints the strips 1004a/1004b and active elements 902 illustrated in FIG. 10. The 3D printer 308 also prints two straps 1104 that extend from each of the strips and are arranged to connect the strips to a base fabric or material. Afterward, the system is integrated into a suitable, wearable material (e.g., a cloth sheet, a jacket, a vest, etc.) that can be easily worn by the user. For example, the wearable material may be made of cloth and the system 310 may be later inserted into, adhered to, mounted on and/or sewn into the wearable material. The connecting of the wearable material and the printed wearable posture advisory system 310 may be performed using conventional techniques (e.g., using an adhesive or stitches, without the assistance of a 3D printer.)

In still other embodiments, the 3D printer 308 is capable of printing out not only the strips and active elements, but also a base material (e.g., a shirt or jacket) into which the system is embedded. That is, a printer is capable of generating a wearable posture advisory system 310 that integrates electronic components with fabrics or wearable materials such that the user can wear the system almost as soon as it is manufactured by the printer. FIG. 12 illustrates an example of this approach. In the example of FIG. 12, the 3D printer 308 prints a wearable posture advisory system 310 that includes the strips 1004a/1004b, the active elements illustrated in FIG. 10 and a base material (e.g., a cloth shirt or jacket) into which the active elements and strips are embedded.

Figure 13:
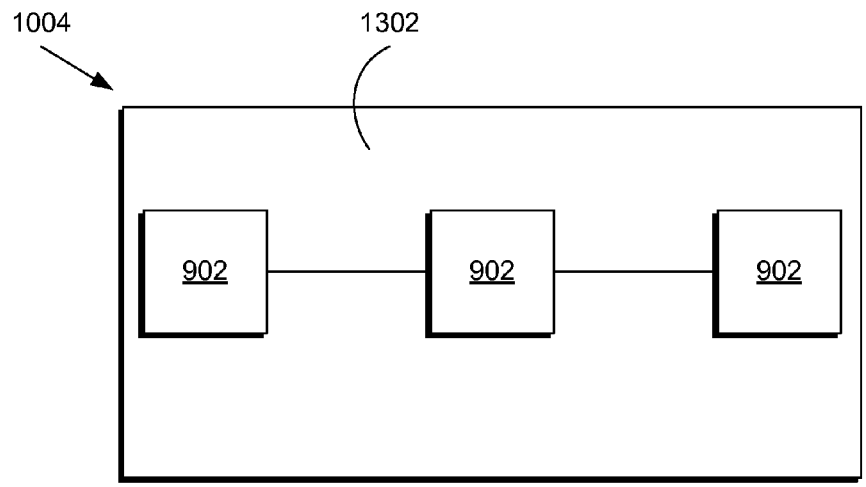
FIG. 13 illustrates a block diagram illustrating a strip of a wearable posture advisory system according to a particular embodiment of the present invention.
Figure 14:
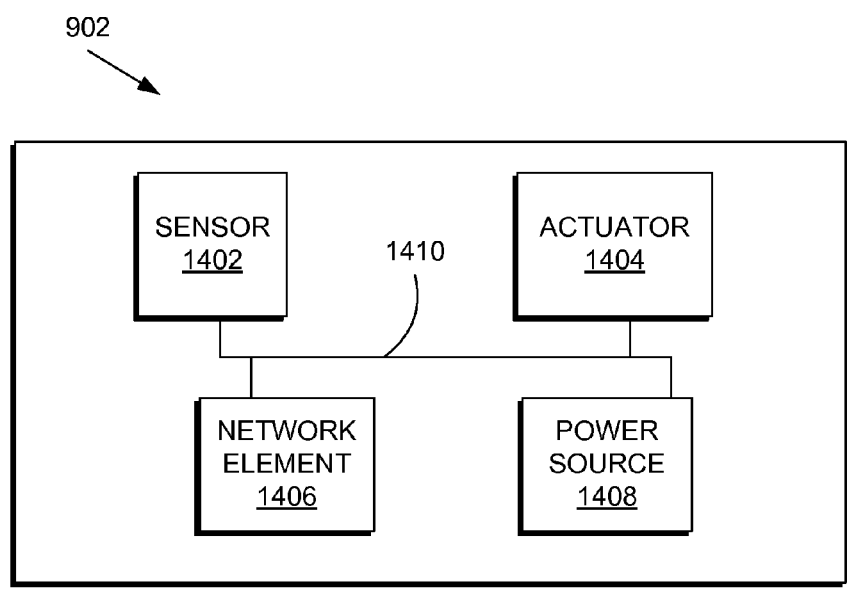
FIG. 14 illustrates a block diagram illustrating an active element according to a particular embodiment of the present invention.

A schematic diagram of each strip 1004 in the wearable posture advisory system 310 is illustrated in FIGS. 13 and 14. In this example, each strip 1004 includes a base material 1302 and one or more active elements 902. In the illustrated embodiment, there are three active elements 902 that are connected in a network via conductive paths. The active elements 902 may be arranged in any suitable manner (e.g., in rows, in an array as in FIG. 9, etc.) The base material 1302 may be made of any suitable material(s) (e.g., cloth, plastic, metal, etc.). It should be appreciated that the strip 1004, base material 1302 and active elements 902 may have any suitable shape, composition, design or dimensions.

FIG. 14 illustrates a schematic diagram of an example active element 902. In the illustrated embodiment, the active element 902 includes a sensor 1402, an actuator 1404, a network element 1406 and a power source 1408. In other embodiments, the active element 902 may include more or less of any of these components.

The sensor 1402 is arranged to help sense or monitor changes in the posture of a user wearing the wearable advisory posture system 310. Any suitable sensor may be used, including but not limited to a pressure sensor and an accelerometer. The actuator 1404 is any software or hardware arranged to emit a signal that prompts the user to change his or her posture. In some embodiments, for example, the actuator 1404 is arranged to vibrate or exert pressure that is felt by the user wearing the system 310.

The network element 1406 is any software or hardware that is arranged to receive data from an external device (e.g., the control device 312) and transmit data to the device. The network element may use any suitable communications protocol or technology to receive and transmit data (e.g., WiFi, Bluetooth, etc.) In various embodiments, for example, the network element 1406 is arranged to transmit data based on sensor data received from the sensor 1402 and/or receive commands for activating the actuator 1404. The sensor 1402, actuator 1404 and network element 1406 are coupled with one another via a network 1410. As a result, data received from the sensor can be sent to the network element 1406 and transmitted, and data received through the network element 1406 can be passed on to the actuator 1404 and/or sensor 1402. The network 1406 also couples each of the aforementioned components to a power source 1408. In some embodiments, multiple strips 1004 and/or active elements 902 are coupled with and transmit/receive data through a shared network element 1406.

The power source 1408 may be any suitable power source that is arranged to provide electrical power to the aforementioned electronic components. In some embodiments, for example, the power source 1408 is a battery. In still other embodiments, the power source 1408 connects with a solar panel, which is located on any suitable exposed portion of the wearable posture advisory system 310 (e.g, on the shoulders, mounted on a hat that worn by the user, etc.). In one approach, for example, the power source 1408 is a battery, which is in turn is connected with and recharged by the aforementioned solar panel. Some implementations include multiple active elements 902 and/or strips 1004 that are all linked using a wired or wireless connection to a shared power source 1408.

It should be noted that in various embodiments, the 3D model 1000 illustrated in FIG. 10 models and indicates all of the aforementioned components of the wearable posture advisory system 310 (e.g., the strip, active element, sensor, actuator, network element, power source, ec.) Using the 3D model 1000, the 3D printer 308 is thus able to print a functioning and complete wearable posture advisory system 310. It should also be noted that the wearable posture advisory system 310 and the active elements 902 may include other components as well e.g., a speaker for emitting audio cues or voices, a user interface or display, etc.

Returning to method 100 of FIG. 1, at step 114, suitable software is provided to the control device 312. The software is installed in a control device 312 that allows the control device 312 to communicate with and control the wearable posture advisory system 310. In some embodiments, the control device 312 downloads the software over a suitable network (e.g., the Internet). In other embodiments, a computer readable storage medium (e.g., a CD, a flash drive, an SD card, etc.) is inserted into the control device 312 and is used to transfer the software into the control device 312. The control device 312 may be any suitable computing device, including but not limited to a smartphone, smartwatch, a wearable device, a personal computer and a laptop computer.

The installed software may include a wide variety of features. Such features include but are not limited to data based on the posture management model, the 3D body model 500 and/or the system model 1000; data regarding the location of components of the system (e.g., the location of actuators, sensors, etc.); unique IDs for each component; mesh data; and communication protocols used to establish a connection with the wearable posture advisory system 310. Generally, the software is stored in a computer readable medium (e.g., hard drive, flash drive, memory etc.) in the control device 312.

At step 116, the control device 312 links to the wearable posture advisory system. That is, the control device 312 connects over a wireless or wired network 316 with the wearable posture advisory system 310. Any suitable network or communications protocol may be used to establish the link e.g., Bluetooth, WiFi, NFC, etc.

The method 100 of FIG. 1 continues with step 202 of method 200 of FIG. 2. At step 202 of FIG. 2, the wearable posture advisory system 310 is worn by the user 302. An example of this is shown in FIG. 10, which illustrates how a wearable posture advisory system 310 may be applied to the lower back or torso of a person. Of course, the wearable posture advisory system 310 may have a wide variety of different forms that are intended to be worn over different parts of the body.

At step 204, the sensor(s) of the wearable posture advisory system collect sensor data. The nature of the sensor data and the data gathering process may vary widely, depending on the design of the sensor(s). In some embodiments, for example, the sensor is an accelerometer that can detect a position of the sensor, which can change as a part of the body that supports the sensor moves or bends. In still other embodiments, the sensor is a pressure sensor that detects pressure, strain and/or tightness of the muscles or skin at a location of the body where the sensor is positioned. As previously noted, the wearable posture advisory system 310 may have multiple sensors that simultaneously collect data from various parts of the body where the sensors are positioned.

At step 206, the wearable posture advisory system 310 transmits the sensor data to the control device 312 (e.g., using the network element 1406) over the network 316. At step 208, the control device 312 receives and processes the sensor data. More specifically, the control device 312 is arranged to analyze the sensor data and, based on the sensor data, determine a current posture of the user (step 210). This analysis may take into account the posture management model described in step 104 of FIG. 1. The control device then determines whether the current posture of the user matches a desired posture (e.g., desired posture of FIG. 5) or a particular alternative posture (e.g., the alternative posture of FIG. 6) that deviates from the healthy, desired posture (step 212).

If the current posture is the desired posture, then the method 200 returns to step 204 and the wearable posture advisory system 310 continues to monitor the posture of the user. If the current posture does not match the desired posture, the method 200 proceeds to step 214. At step 214, the control device determines a corrective action that will help transition the user from the alternative posture to the desired posture (e.g., based on the posture management model.)

The corrective action may vary widely, depending on the current posture and the desired posture. In various embodiments, the software installed in the control device 312 stores multiple possible alternative postures, as well as corresponding corrective actions for each posture that help the user revert to the desired posture. The corrective actions typically include commands that cause the actuators to take a particular action, as will be described in greater detail below.

At step 216, the control device 312 transmits control data to the wearable posture advisory system 310. Afterward, the actuator(s) of the wearable posture advisory system 310 perform an action in response to the transmitted control data.

The type of action that the actuator(s) may perform may differ, depending on the current posture and the correction action determined by the control device 312. In various embodiments, for example, the actuator generates a physical stimulus that can be felt by the user. The physical stimulus is arranged to prompt to the user to shift their posture from the alternative posture to the desired, more healthy posture (e.g., as indicated by the corrective action of the posture management model.)

Consider an example where the user is leaning on his or her elbow too far towards the left as indicated in FIG. 7. This causes an unhealthy curve in the spine. In some embodiments, the control data causes actuators arranged along the spine to vibrate or generate pressure that is felt by the user, so the user is reminded to straighten his or her spine. Alternatively, the actuators that are situated on the left side of the spine are activated in this manner, to remind the user that the left side is under too much strain and should be straightened. The actuators may be activated to issue a physical stimulus in any combination or sequence (e.g., multiple actuators may be activated simultaneously, in any suitable pattern, in sequence along a line one after the other, vibrate in pulses that follow a particular pattern, etc.)

The wearable posture advisory system 310 may prompt the user to correct his or her posture using other methods as well. Some designs involve the actuator emitting a vibration, pressure and/or heat. In some implementations, for example, the wearable posture advisory system 310 and/or the control device 312 emit an audible sound e.g., a chime, ring or voice, which reminds the user to correct their posture. In addition or alternatively, the control device 312 displays a message on a user interface or screen, indicating to the user that his or her posture should be corrected.

The magnitude and nature of the corrective action and the actuator operation may vary depending on the sensor data received from the wearable posture advisory system 310. In various embodiments, for example, the control device 312 stores data or a posture management model indicating a normal posture and one or more alternative postures (e.g., as discussed in connection with steps 104 and 114 of FIG. 1) Each posture is associated with a particular position for each sensor in the wearable advisory system 310 (e.g., the desired posture position for a sensor is the position that the sensor would be in when the user is wearing the system 310 and is in the desired posture.) The control device 312 receives the sensor data (steps 204, 206 and 208) and determines the current location of each sensor based on the sensor data. Additionally, the control device 312 determines how much the current location of each sensor deviates from its corresponding desired posture position and/or the direction of the deviation, if any. In some embodiments, the control device 312 uses a mesh (e.g., mesh 800 of FIG. 8) overlaid over a 3D body model to help determine any changes in the position/posture of the user based on sensor data received from a sensor in a particular cell 802. The control device 312 then determines a corrective action based on this deviation and direction information (step 214).

To help illustrate an embodiment of the above approach, consider an example in which there is a wearable posture advisory system 310 that is worn by a user. The system 310 positions one sensor on the upper back and one on the lower back. A control device 312 (e.g., a smartphone, a smartwatch, etc.) stores data indicating a desired posture position for the upper and lower back sensors. That is, the desired posture positions for the upper and lower back sensors are the positions that the sensors are in when the user is wearing the system 310 and is in the desired position (e.g., standing or sitting straight in a healthy manner.) The control device 312 receives sensor data from the sensors, indicating that the current positions of the sensors have deviated from their corresponding desired posture positions. Based on the sensor data, the control device 312 determines that the lower back sensor has shifted slightly forward and the upper back sensor has shifted even more forward and lower relative to its desired posture position, indicating that the user is bending or hunching over in an unhealthy manner (steps 204, 206 and 208). The control device 312 transmits a signal to the system 310 (step 214 and 216). In response to and based on the signal, the actuators in the system 310 indicate to the user (e.g., using a physical stimulus, heat, pressure, vibration, etc.) that he or she should straighten his or her posture. That is, in some embodiments, based on the above deviation and direction data, the physical stimulus or signal applied by the actuators indicate a particular direction that the user should move or bend. Also, the strength of the actuator signal/stimulus may vary based on the amount of the deviation (e.g., if the user is hunched over a great deal, the strength of the physical stimulus may be much greater than if the user is hunched over only slightly) in order to more strongly and urgently prompt the user to change his or her posture.

Once the corrective control data has been received at the wearable posture advisory system 312 and the user has been prompted, the method 200 returns to step 204. The sensors of the system continue to monitor the user's posture and the method repeats steps 204-218.

Some approaches involve a specialist using the control device 312 and the printed wearable posture advisory system 310 to revisit or perform some of the steps in method 100 of FIG. 1. In some implementations, for example, the specialist will place the printed system 310 onto the user 302. The specialist then utilizes the control device 312 to examine the user's posture. For example, the specialist may ask the user 302 to stand, sit and assume various other poses while receiving feedback from the control device 312 on the posture of the user as he or she is in these poses (e.g., as described in method 200 of FIG. 2.) In some embodiments, detailed information on the posture of the user (e.g., whether the posture meets the desired posture or is an alternative posture) will appear on a user interface/display on the control device 312. Based on this feedback, the specialist can adjust any aspect of the posture management model (e.g., what constitutes a desired posture, an alternative posture or a correction action) at the modeling device 306 and/or the control device 312. In this manner, the specialist can use the wearable posture advisory system 310 to further configure the system and tailor it to the user.

Figure 15:
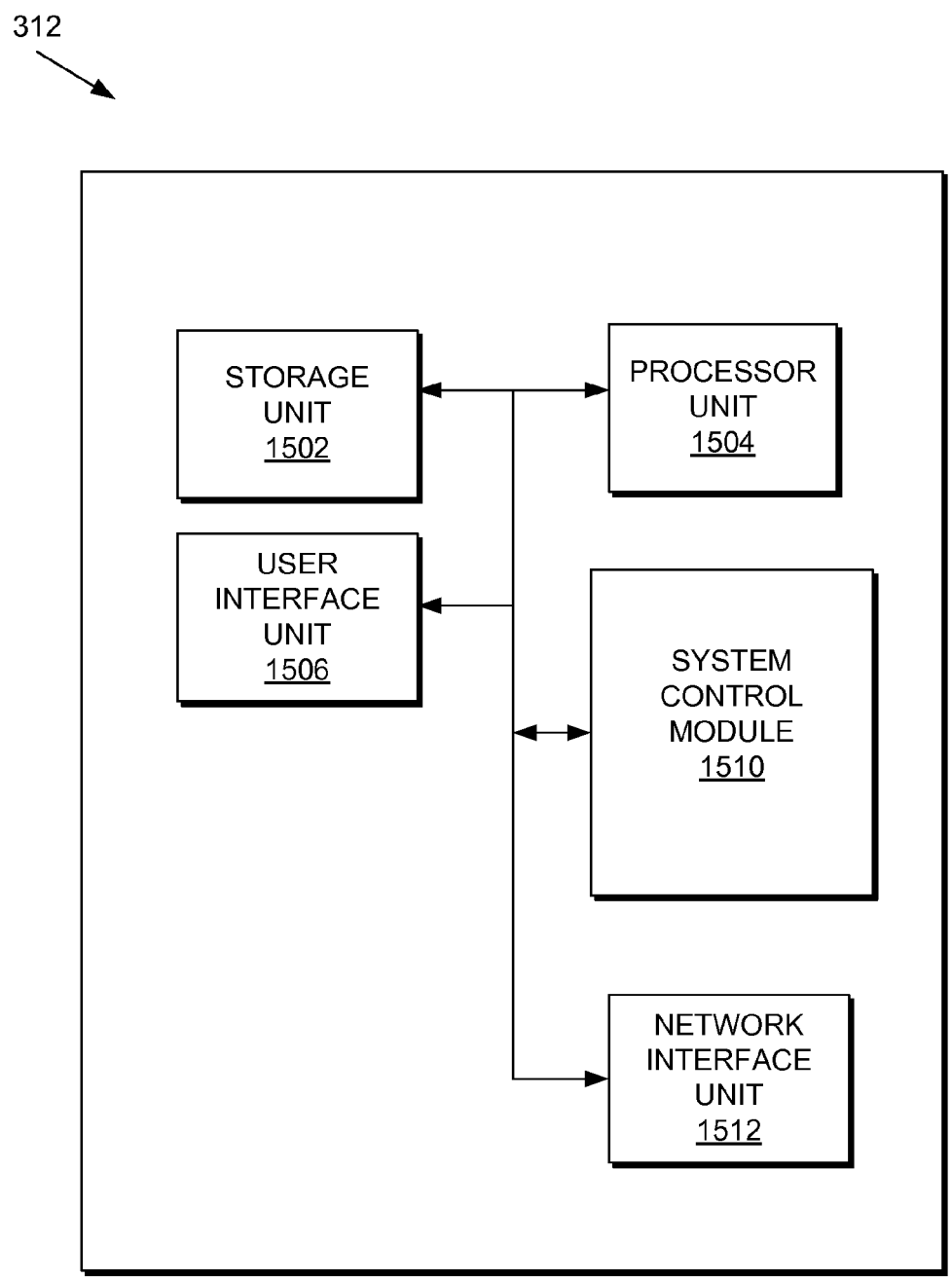
FIG. 15 is a block diagram illustrating a control device according to a particular embodiment of the present invention.

Referring next to FIG. 15, a control device (e.g., control device 312 of FIG. 3) according to a particular embodiment of the present invention will be described. The control device 312 includes a processor unit 1504 that includes one or more processors, a storage unit 1502, a system control module 1510, a user interface unit 1506, and a network interface unit 1512. The control device 312 may be any suitable computing device, including but not limited to a smartphone, a portable device, a computer tablet, a desktop computer, a laptop, computer glasses, smartwatch and/or any type of wearable or mobile technology.

The network interface unit 1112 includes any hardware or software suitable for enabling the device 312 to communicate with the wearable posture advisory system 310 over the network 316. In some embodiments, the network interface unit 1512 is also arranged to receive software or applications (e.g, over the Internet or any other suitable network) that can be installed at the control device 312 (e.g., as discussed in connection with step 114 of FIG. 1.) In still other embodiments, the network interface unit 1512 is arranged to receive data (e.g., the posture management model) from the modeling device 306. The network interface unit 1512 is arranged to transmit data and receive data using any suitable network (e.g., LAN, Internet, etc.) or communications protocol (e.g., Bluetooth, WiFi, NFC, etc.)

The storage unit 1502 is any hardware or suitable for storing data or executable computer code. The storage unit 1502 can include but is not limited to a hard drive, flash drive, non-volatile memory, volatile memory or any other type of computer readable storage medium. Any operation or method for the control device 312 that is described in this application (e.g., steps 204-216 of FIG. 2) may be stored in the form of executable computer code or instructions in the storage unit 1102. The execution of the computer code or instructions by the processor unit 1504 causes the device 312 to perform any of the aforementioned operations or methods.

The system control module 1510 is any hardware or software arranged to perform any of the operations or methods (e.g., steps 204-216 of FIG. 2) described in this application that pertain to the control device 312. In various embodiments, the system control module 1510 is arranged to receive sensor data from the wearable posture advisory system 310, determine a current posture of the user, determine a corrective action and transmit control data to the system 310. In some embodiments, the system control module 312 takes the form of a mobile application that is downloaded into the control device over the Internet from an online store (e.g., Google Play, the Apple App Store, etc.)

The user interface unit 1506 is any hardware or software for presenting a user interface to the user of the device 312. In various embodiments, the user interface unit 1506 includes but is not limited to a mouse, a keyboard, a touch-sensitive (capacitive) screen, a video display, an e-ink display, an LCD screen, an OLED screen and a heads up display. The user interface 1106 may also be capable of receiving audio commands and making audio statements. In various implementations, the user interface unit 1506 displays an interface used to manage the installation of software (e.g., as discussed in step 114 of FIG. 1) and/or display a message or diagram that prompts a user to correct his or her posture (e.g., as discussed in connection with 218 of FIG. 2.) A specialist or user may use the user interface to adjust or operate software (e.g., a posture management model) stored in the device.

Figure 16:
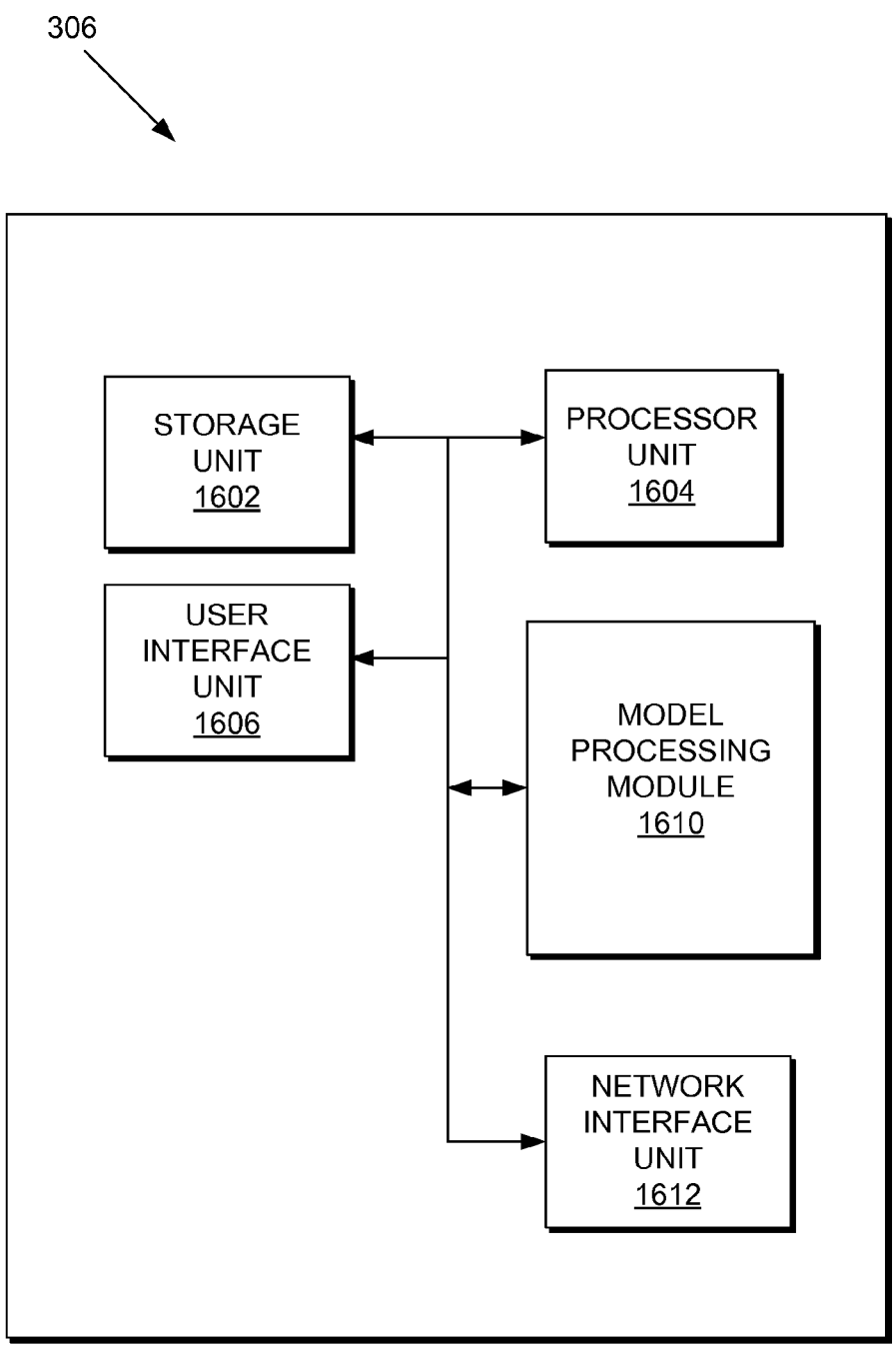
FIG. 16 is a block diagram illustrating a modeling device according to a particular embodiment of the present invention.

Referring next to FIG. 16, a modeling device 306 (e.g., modeling device 306 of FIG. 3) according a particular embodiment of the present invention will be described. The modeling device 306 includes a processor unit 1604 that includes one or more processors, a storage unit 1602, a model processing module 1610, a user interface unit 1606, and a network interface unit 1612. The modeling device 306 may be any suitable computing device, including but not limited to a terminal, a computer, a smartphone, a portable device, a computer tablet, a laptop, computer glasses, smartwatch and/or any type of wearable or mobile technology.

The network interface unit 1612 includes any hardware or software suitable for enabling the device 306 to communicate with the control device 312 and/or the 3D scanner 304. The network interface unit 1112 is arranged to transmit data to and receive data from the control device 312 and/or the 3D scanner 304 using any suitable network (e.g., LAN, Internet, etc.) or communications protocol (e.g., Bluetooth, WiFi, etc.) In some embodiments, the data transfer takes place through use or insertion of a computer readable storage medium (e.g., use of a flash drive, CD, SD card, etc.) rather than through a network.

The storage unit 1602 is any hardware or suitable for storing data or executable computer code. The storage unit 1602 can include but is not limited to a hard drive, flash drive, non-volatile memory, volatile memory or any other type of computer readable storage medium. Any operation or method for the modeling device 306 that is described in this application (e.g., steps 102-110 of FIG. 1) may be stored in the form of executable computer code or instructions in the storage unit 1602. The execution of the computer code or instructions by the processor unit 1604 causes the device 306 to perform any of the aforementioned operations or methods.

The model processing module 1610 is any hardware or software arranged to perform any of the operations or methods (e.g., steps 102-110 of FIG. 1) described in this application that pertain to the model processing device. In various embodiments, the model processing module 1610 is arranged to receive data from a 3D scanner, generate a body model, a posture management model and/or a system model and/or transmit the system model to the 3D printer.

The user interface unit 1606 is any hardware or software for presenting a user interface to the user of the device 306. In various embodiments, the user interface unit includes but is not limited to a mouse, a keyboard, a touch-sensitive (capacitive) screen, a video display, an e-ink display, an LCD screen, an OLED screen and a heads up display. In various implementations, the user interface unit 1606 displays an interface used to manage the generation of the aforementioned models. In some embodiments, a specialist (e.g., a physical therapist) can interact with the interface to help adjust or customize the posture management model for a particular user (e.g., as described in connection with step 104 of FIG. 1.)

The methods 100 and 200 of FIGS. 1-2 describe an example in which particular operations are performed by the modeling device or the control device. It should be appreciated that these operations may be performed by any number of devices. In some embodiments, for example, the modeling device and the control device are the same device. In still other embodiments, their features and functionality are divided among a greater number of devices. In various implementations, for example, the 3D body model is generated by one device; the posture management model is generated by another device; the system model is generated by a third device; and the control device is separate from the other devices.

Any of the methods or operations described herein can be stored in a tangible computer readable medium in the form of executable software code. The code can then be executed by one or more processors. The execution of the code causes a corresponding device (e.g., modeling device 306, control device 312, etc.) to perform the described operations.

Although only a few embodiments of the invention have been described in detail, it should be appreciated that the invention may be implemented in many other forms without departing from the spirit or scope of the invention. For example, the present application and figures describe various methods (e.g., methods 100 and 200 of FIGS. 1-2) that perform particular operations. It should be appreciated that in some embodiments, one or more of these operations/steps may be modified, reordered and/or deleted. Additionally, some figures, such as FIGS. 3 and 13-16, describe devices that contain various components. It should be noted that in some embodiments, one or more of these components may be merged together. In still other embodiments, one or more components may be separated into a greater number of components. The features of one component may be transferred to another and/or modified as appropriate. Each device may have additional components beyond what is shown in the corresponding figure. Therefore, the present embodiments should be considered illustrative and not restrictive and the invention is not to be limited to the details given herein.

What is claimed is:

1. A method for formulating a wearable posture advisory system, the method comprising:
retrieving a three-dimensional (3-D) system model indicating one or more sensors that are arranged to help determine a posture of a user of the wearable posture advisory system and one or more actuators that are arranged to help instruct the user to adjust the posture, wherein the 3-D system model is generated based on a 3-D body model of at least a part of a body of the user and the 3-D body model is obtained via scanning at least the part of the body of the user using a 3-D scanner, wherein the 3-D body model includes a mesh defining a plurality of cells on the 3-D body model with each cell being a region on the 3-D body model that is identified by one or more coordinates, wherein at least one of the cells indicates a location for one of the actuators or sensors of the 3-D system model; and
manufacturing the wearable posture advisory system using the 3-D system model, wherein the wearable posture advisory system includes the one or more sensors and the one or more actuators indicated in the 3-D system model and includes said one of the actuators or sensors based upon said location.

2. The method of claim 1 wherein the cells are one or more of 1) distributed unevenly across the 3D body model; 2) vary in size and 3) are positioned in an asymmetrical arrangement.

3. The method of claim 1 wherein:
the 3D system model models one or more strips, each strip including one or more active pads wherein each active pad includes one or more of a sensor, an actuator, a solar panel, a battery and a network element arranged to communicate with a remote device; and
each sensor is an accelerometer that is arranged to help determine the posture of the user.

4. The method of claim 1 further comprising:
generating a posture management model based at least in part on the 3D body model wherein the posture management model helps define a desired posture for the user, an alternative posture for the user that deviates from the desired posture, and a corrective action that indicates how the user can transition from the alternative posture to the desired posture.

5. The method of claim 4 wherein:
the posture management model is stored at a computing device; and
the method further comprises receiving input from a specialist at the computing device wherein the input causes adjustments in the posture management model and customizes the posture management model for the user.

6. The method of claim 4 further comprising:
providing software based on the posture management model; and
installing the software at a control device wherein the software is arranged to process sensor data received at the control device from the wearable posture advisory system after the wearable posture advisory system is manufactured based on the 3D system model, the received data indicating a current posture of the user and wherein the software is further arranged to help transmit signals to the manufactured wearable advisory system indicating the corrective action that the user should undertake to improve the current posture.

7. The method of claim 4 further comprising:
receiving sensor data from one or more sensors in the wearable posture advisory system after the wearable posture advisory system is manufactured based on the 3D system model and placed on the user; and
using the sensor data to help determine the posture management model.

8. The method of claim 4 further comprising:
installing software based on the posture management model at a control device;
receiving signals from the one or more sensors of the wearable posture advisory system at the control device after the wearable posture advisory system is manufactured based on the 3D system model wherein the signals help indicate the posture of the user; and
transmitting signals from the control device to the manufactured wearable advisory system that cause the one or more actuators to prompt the user to correct the current posture.

9. The method of claim 8 wherein:
the prompting of the user includes generating, at the one or more actuators, a physical stimulus, the physical stimulus being selected from one or more of vibration, heat and pressure.

10. The method of claim 9 further comprising:
after the wearable posture advisory system is manufactured based on the 3D system model, placing the manufactured wearable posture advisory system on the user such that the one or more sensors of the system are distributed in an asymmetrical arrangement on the user.

11. The method of claim 1 wherein said manufacturing includes printing the wearable posture advisory system using a 3-D printer.

* * * * *